US012560602B2

(12) United States Patent
Park et al.

(10) Patent No.: US 12,560,602 B2
(45) Date of Patent: Feb. 24, 2026

(54) DIAGNOSTIC CARTRIDGE FOR IMMUNODIAGNOSIS AND DIAGNOSTIC DEVICE AND SYSTEM USING THE SAME

(71) Applicant: BODITECH MED INC., Chuncheon-si (KR)

(72) Inventors: Dae Gyun Park, Seoul (KR); Minseok Cha, Chuncheon-si (KR); Ha Yong Song, Chuncheon-si (KR)

(73) Assignee: BODITECH MED INC., Chuncheon-si (KR)

( * ) Notice: Subject to any disclaimer, the term of this patent is extended or adjusted under 35 U.S.C. 154(b) by 538 days.

(21) Appl. No.: 18/323,723

(22) Filed: May 25, 2023

(65) Prior Publication Data

US 2024/0085410 A1     Mar. 14, 2024

Related U.S. Application Data

(63) Continuation of application No. PCT/KR2021/014684, filed on Oct. 20, 2021.

(30) Foreign Application Priority Data

Nov. 26, 2020     (KR) ........................ 10-2020-0161193

(51) Int. Cl.
  *G01N 33/543* (2006.01)
  *G01N 21/64* (2006.01)
  *G01N 21/84* (2006.01)

(52) U.S. Cl.
  CPC ... *G01N 33/54388* (2021.08); *G01N 21/6454* (2013.01); *G01N 21/6486* (2013.01);
  (Continued)

(58) Field of Classification Search
  CPC ......... G01N 33/54388; G01N 21/6454; G01N 21/6486; G01N 21/8483; G01N 2021/6463; G01N 2201/0221; G01N 2201/0256; G01N 21/78; G01N 2021/7786; G01N 33/543; G01N 33/5302; G01N 33/558; G01N 33/54387; G01N 33/54389; G01N 2021/7759; B01L 3/00; B01L 2200/04; B01L 2300/021; B01L 2300/027;
  (Continued)

(56) References Cited

U.S. PATENT DOCUMENTS 10,799,861 B2     10/2020   Paek
2017/0010261 A1     1/2017   Hand et al.
(Continued)

FOREIGN PATENT DOCUMENTS

JP          2017-505915 A     2/2017
KR          10-0616426 B1     8/2006
(Continued)

OTHER PUBLICATIONS

International Search Report issued in PCT/KR2021/014684; mailed Mar. 4, 2022.

*Primary Examiner* — Christopher L Chin

(74) *Attorney, Agent, or Firm* — Studebaker Brackett PLLC

(57)          ABSTRACT

The present disclosure relates to a diagnostic cartridge for immunodiagnosis, and a reader and a diagnostic system using the same. A diagnostic cartridge, including the diagnostic pad and the color reaction pad, is provided to detect a color reaction and a fluorescence reaction through the single diagnostic cartridge.

11 Claims, 7 Drawing Sheets

(52) U.S. Cl.
CPC . *G01N 21/8483* (2013.01); *G01N 2021/6463*
(2013.01); *G01N 2201/0221* (2013.01); *G01N*
*2201/0256* (2013.01)

(58) Field of Classification Search
CPC ............. B01L 2300/069; B01L 3/5023; B01L
2300/0825; G06K 7/14
USPC ....... 422/400, 401, 403, 404, 420, 421, 425,
422/426, 430, 82.05, 554; 435/287.7,
435/287.9, 970, 805, 810; 436/169, 170,
436/172, 514, 518, 530, 810
See application file for complete search history.

(56) References Cited

U.S. PATENT DOCUMENTS

| | | | |
|---|---|---|---|
| 2018/0141041 | A1 | 5/2018 | Paek |
| 2021/0318301 | A1 | 10/2021 | Nahm et al. |

FOREIGN PATENT DOCUMENTS

| | | |
|---|---|---|
| KR | 10-2009-0006999 A | 1/2009 |
| KR | 10-2018-0058646 A | 6/2018 |
| KR | 10-2102773 B1 | 4/2020 |
| KR | 10-2020-0055913 A | 5/2020 |

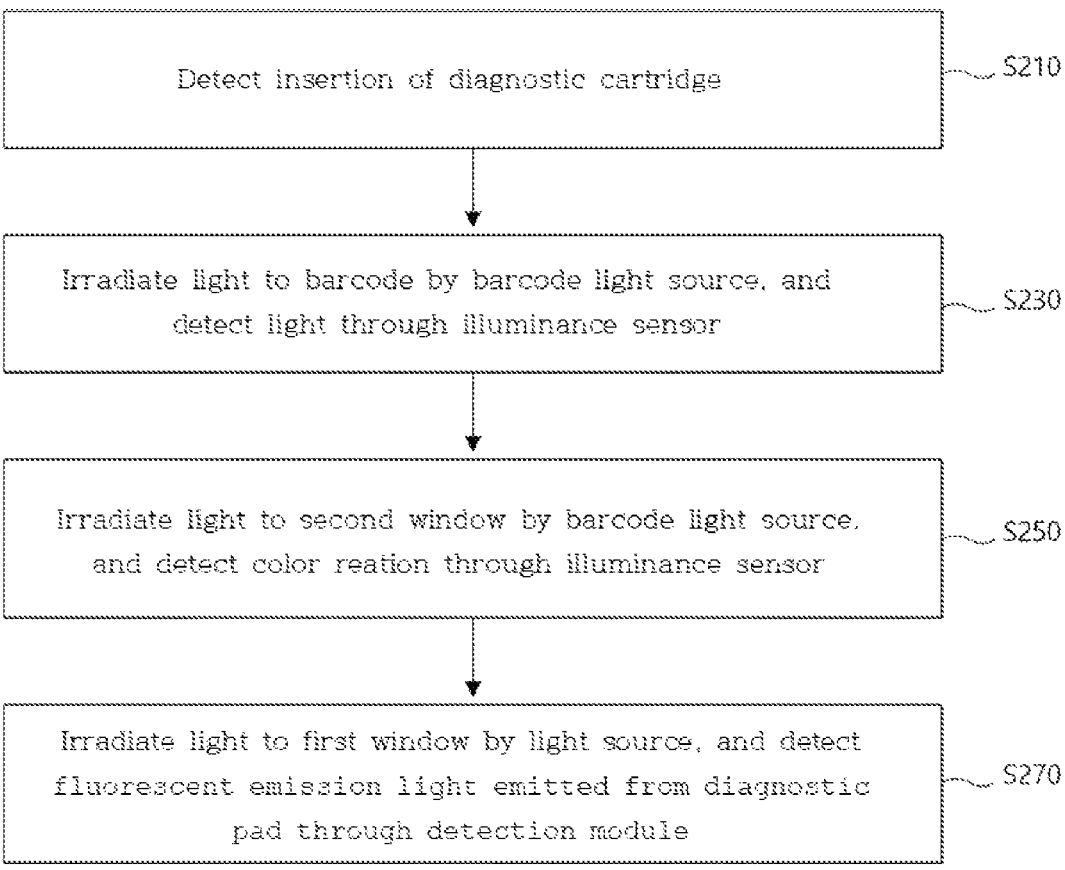

Detect insertion of diagnostic cartridge ————— S210

Irradiate light to barcode by barcode light source, and detect light through illuminance sensor ————— S230

Irradiate light to second window by barcode light source, and detect color reation through illuminance sensor ————— S250

Irradiate light to first window by light source, and detect fluorescent emission light emitted from diagnostic pad through detection module ————— S270

DIAGNOSTIC CARTRIDGE FOR IMMUNODIAGNOSIS AND DIAGNOSTIC DEVICE AND SYSTEM USING THE SAME

CROSS-REFERENCE TO RELATED APPLICATION

The present application is a continuation of International Patent Application No. PCT/KR2021/014684, filed on Oct. 20, 2021, which is based upon and claims the benefit of priority to Korean Patent Application No. 10-2020-0161193, filed on Nov. 26, 2020. The disclosures of the above-listed applications are hereby incorporated by reference herein in their entirety.

BACKGROUND

1. Technical Field

The present disclosure relates to a diagnostic cartridge for immunodiagnosis, and a reader and a diagnostic system using the same, and more specifically, to a diagnostic cartridge which can detect a fluorescence reaction and a color reaction of a sample using a single reader.

2. Description of Related Art

Various diagnostic kits detecting specific target substances in liquid samples, such as blood samples, have been developed, and they make it possible for convenient and fast disease diagnosis. In particular, diagnostic kits based on immunochromatographic analysis are widely used to detect diseases or to understand the spread of disease, and are being developed as methods for easily testing a small amount of biological substances in various fields as well as biological and environmental ones.

In such diagnostic kits, fluorescent substances are used as marking substances for the detection of target substances, and fluorescence readers which read fluorescent signals and color readers which detect color reactions are mainly used.

Specifically, clinical chemistry reagents detect absorbance signals before and after the reaction as the color reactions using enzymes/substrates, and quantify the degree of the reaction. Moreover, quantitative immunoassay reagents detect fluorescence and luminescence signals occurring during the formation of antigen/antibody complexes using antigen/antibody reactions, and quantify the antigens/antibodies.

As described above, the two detection methods can detect reactions to different reagents. However, due to the differences in detection methods, it is difficult to realize a compact tester having both of the two detection methods.

Therefore, there is a need to develop a diagnostic cartridge and reader that can provide functions to detect both of the color reaction and the fluorescence reaction, but currently, such technology is not publicly available.

SUMMARY

The present disclosure has been made to solve the above-mentioned problems occurring in the prior art, and in an aspect of the present disclosure, an object of the present disclosure is to provide a diagnostic cartridge, including a diagnostic pad and a color reaction pad to detect a color reaction and a fluorescence reaction In addition, another object of the present disclosure is to provide an immunodiagnostic reader detecting a barcode of the diagnostic cartridge and detecting the color reaction of the color pad using a barcode light source, and detecting the fluorescence reaction of the diagnostic pad using another light source.

Furthermore, a further object of the present disclosure is to provide an immunodiagnostic reader using one barcode light source for multiple purposes by adjusting the light quantity when the barcode light source detects the barcode and when the barcode light source detects the color reaction of the color pad.

The aspects of the present disclosure are not limited to those mentioned above, and other aspects not mentioned herein will be clearly understood by those skilled in the art from the following description.

To accomplish the above-mentioned objects, according to an aspect of the present disclosure, there is provided an immunodiagnostic system performing immunodiagnosis using a diagnostic cartridge inserted into a reader, including: a diagnostic cartridge; and a reader, wherein the diagnostic cartridge includes: sample inlets located in different positions on the upper surface; a case having a first window for fluorescence measurement and a barcode and a pad part located on a support within the case, wherein the pad part includes: a sample pad allowing a sample inserted into the sample inlet to move; a coloration pad arranged to correspond to the position of the sample inlet on the sample pad; and a diagnostic pad located at the end of the sample pad and arranged to correspond to the position of the first window to detect emitted fluorescence, wherein the reader includes: an insertion space into which the diagnostic cartridge is inserted; a driving module moving an optical module, including a light source and a barcode light source located in different positions; and a control unit, which when insertion of the diagnostic cartridge into the insertion space is detected, controls the driving module to move the barcode light source to the barcode position of the diagnostic cartridge to control irradiation of a first amount of light toward the barcode, recognizes the type of the diagnostic cartridge and the type of the sample based on the light detected from the barcode through an illuminance sensor, loads position information of the sample inlet and the first window according to the recognized type of the diagnostic cartridge, controls the driving module to move the barcode light source to the position of the sample inlet corresponding to the sample pad position of the diagnostic cartridge to control irradiation of a second amount of light, which is less than the first amount of light, in a direction of the sample inlet, and detects the color reaction of the coloration pad through the illuminance sensor.

In this instance, after detecting the color reaction of the coloration pad, the control unit controls the driving module to move the light source to the position of the first window, which corresponds to the position of the diagnostic pad in the diagnostic cartridge, and controls it to irradiate light toward the first window, and detects the fluorescence emitted from the diagnostic pad.

Moreover, the diagnostic pad includes a fluorescent material, which can detect fluorescent signals or luminescent signals when an antigen-antibody complex is formed using an antigen-antibody reaction for a quantitative immunoassay reagent, and a fluorescent reaction is caused by the sample moved through the sample pad.

Furthermore, the insertion space includes a sensor which detects the insertion of the diagnostic cartridge, and the optical module further includes a light guide unit to guide light irradiated from the light source.

Additionally, the pad part further includes an absorption pad arranged to contact the other end of the diagnostic pad.

In another aspect of the present invention, there is provided an immunodiagnostic system performing immunodiagnosis using a diagnostic cartridge inserted into a reader, including: a diagnostic cartridge; and a reader, wherein the diagnostic cartridge includes: first windows for fluorescence measurement, located in different positions on the upper surface; a case having a second window for coloration measurement, a sample inlet for inserting sample and a barcode; and a pad part located on a support within the case, wherein the pad part includes: a diagnostic pad arranged to correspond to the position of the first window; a coloration pad arranged to correspond to the position of the second window; and a sample pad which enables the sample inserted into the sample inlet to move toward the coloration pad and the diagnostic pad, wherein the reader includes: an insertion space into which the diagnostic cartridge is inserted; a driving module moving an optical module, including a light source and a barcode light source located in different positions; and a control unit, which, when insertion of the diagnostic cartridge into the insertion space is detected, controls the driving module to move the barcode light source to the barcode position of the diagnostic cartridge to control irradiation of a first amount of light toward the barcode, recognizes the type of the diagnostic cartridge and the type of the sample based on the light detected from the barcode through an illuminance sensor, loads position information of the first window and the second window according to the recognized type of the diagnostic cartridge, controls the driving module to move the barcode light source to the position of the second window corresponding to the coloration pad position of the diagnostic cartridge to control irradiation of a second amount of light, which is less than the first amount, in a direction of the second window, and detects the color reaction of the coloration pad through the illuminance sensor.

In this instance, the sample pad has one end arranged to contact the coloration pad and the other end arranged to contact the diagnostic pad, such that the sample inserted into the sample inlet is moved to the coloration pad and the diagnostic pad.

In addition, the sample pad includes: a first sample pad, which is disposed in a position corresponding to the position of the sample inlet and allows a sample inserted into the sample inlet to move to the coloration pad, which is placed to contact a lower portion of one end; and a second sample pad, of which one end is arranged to contact a lower portion of the other end of first sample pad and the other end is arranged to contact one end of the diagnostic pad, and wherein the pad part further comprises an absorption pad arranged to contact the other end of the diagnostic pad.

BRIEF DESCRIPTION OF THE DRAWINGS

FIGS. 9 and 10 are flow charts of an immunodiagnostic method according to an embodiment of the present disclosure.

DETAILED DESCRIPTION

Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms. The exemplary embodiments are provided so that the present disclosure is completely disclosed, and a person of ordinary skilled in the art can fully understand the scope of the present disclosure. Therefore, the present disclosure will be defined only by the scope of the appended claims.

Terms used in the specification are used to describe specific embodiments of the present disclosure and are not intended to limit the scope of the present disclosure. In the specification, the terms of a singular form may include plural forms unless otherwise specified. It should be also understood that the terms of 'include' or 'have' in the specification are used to mean that there is no intent to exclude existence or addition of other components besides components described in the specification. In the detailed description, the same reference numbers of the drawings refer to the same or equivalent parts of the present disclosure, and the term "and/or" is understood to include a combination of one or more of components described above. It will be understood that terms, such as "first" or "second" may be used in the specification to describe various components but are not restricted to the above terms. The terms may be used to discriminate one component from another component. Therefore, of course, the first component may be named as the second component within the scope of the present disclosure.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

Hereinafter, preferred embodiments of the present disclosure will be described in detail with reference to the accompanying drawings.

Figure 1:
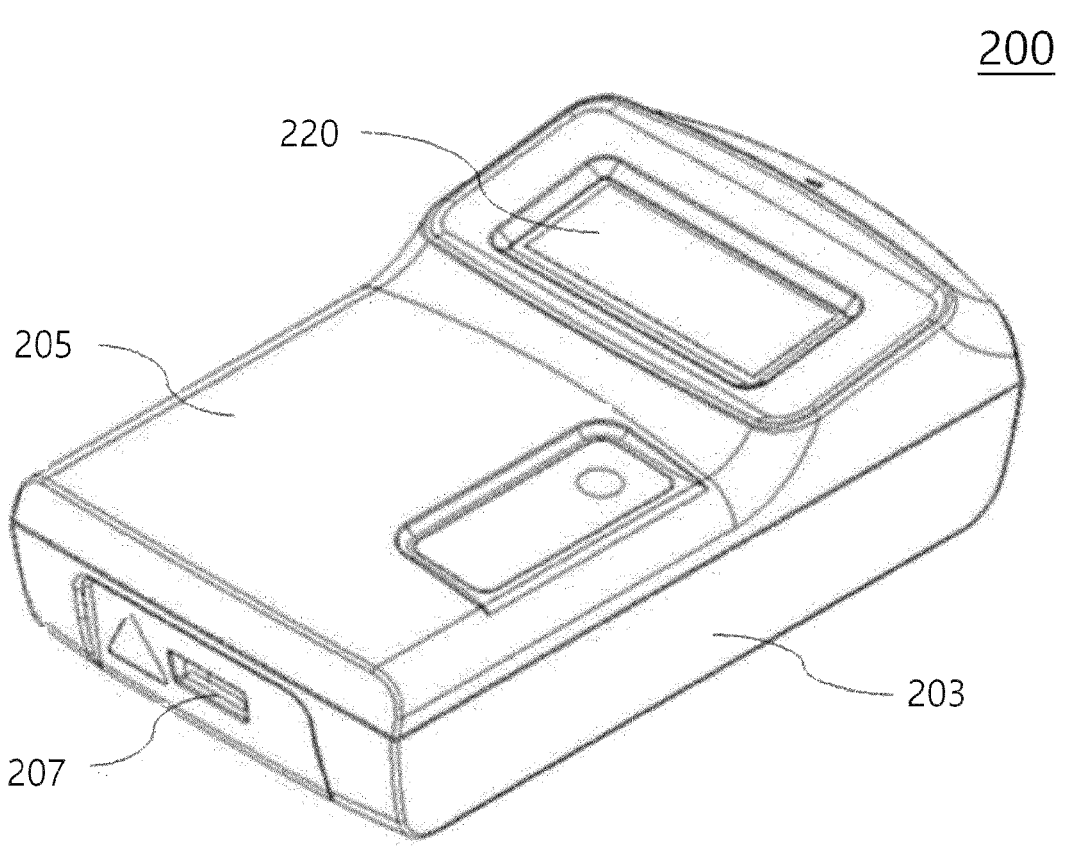
FIG. 1 is a diagram illustrating an immunodiagnostic reader according to an embodiment of the present disclosure.

FIG. 1 is a diagram illustrating an immunodiagnostic reader according to an embodiment of the present disclosure.

Figure 2:
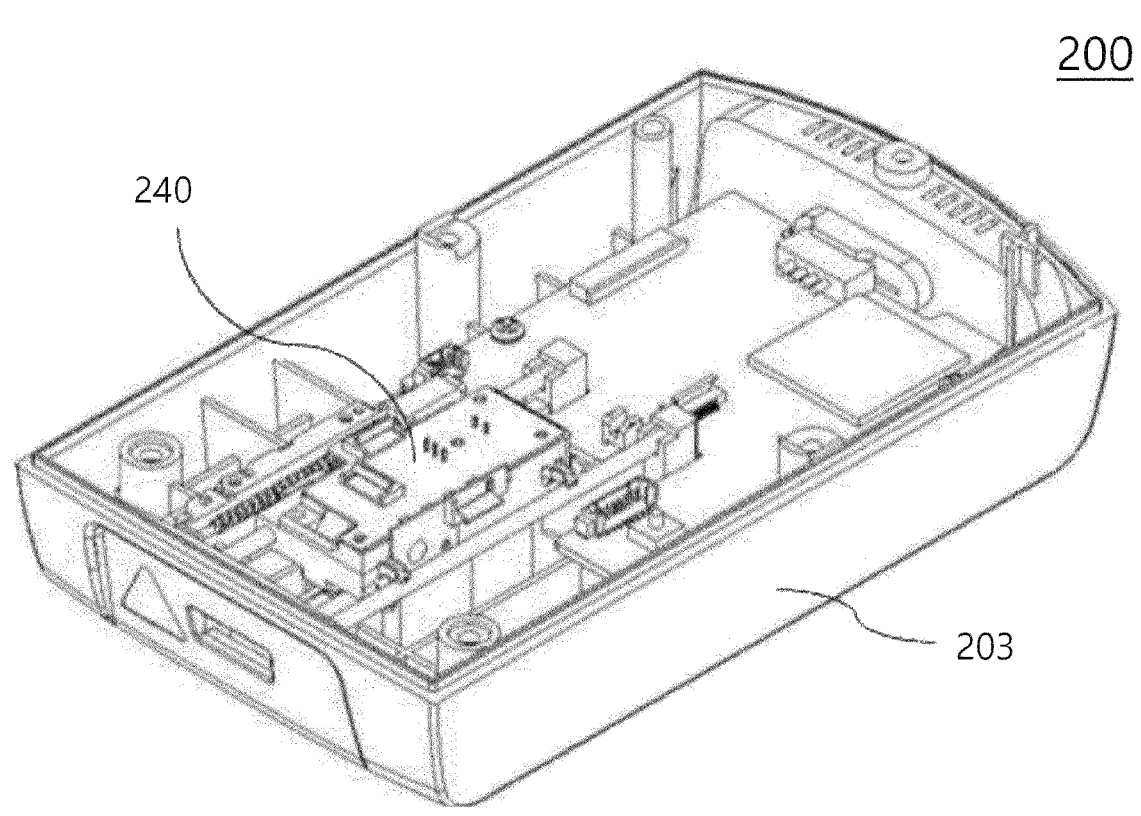
FIG. 2 is a diagram illustrating an optical module of the immunodiagnostic reader according to an embodiment of the present disclosure.

FIG. 2 is a diagram illustrating an optical module of the immunodiagnostic reader according to an embodiment of the present disclosure.

Referring to FIGS. 1 and 2, the immunodiagnostic reader 200 according to the embodiment of the present disclosure includes an upper frame 205 and a lower frame 203 which are combined with each other, and the upper frame 205 has a display unit 220 formed thereon, which can display the operating status, operational results, and detection results of the immunodiagnostic reader 200 through a display module.

In this instance, the display unit 220 may be formed on the upper frame 205 as illustrated in FIG. 1, but is not limited thereto, and may also be formed as a separate frame, or may be a display window of an external device.

The lower frame 203 has an insertion part formed thereon into which a diagnostic cartridge 100 can be inserted.

Moreover, although not illustrated in the drawing, the reader 200 has an insertion space formed extending from the insertion part, allowing the diagnostic cartridge 100 to be inserted into the insertion part.

As illustrated in FIG. 2, an optical module 240 is provided inside the reader 200.

As an embodiment, inside the frame of the reader 200, a connector to which a certain electrical device, a power device, and so on can be connected may be provided, and a battery that can supply power may be equipped.

Figure 3:
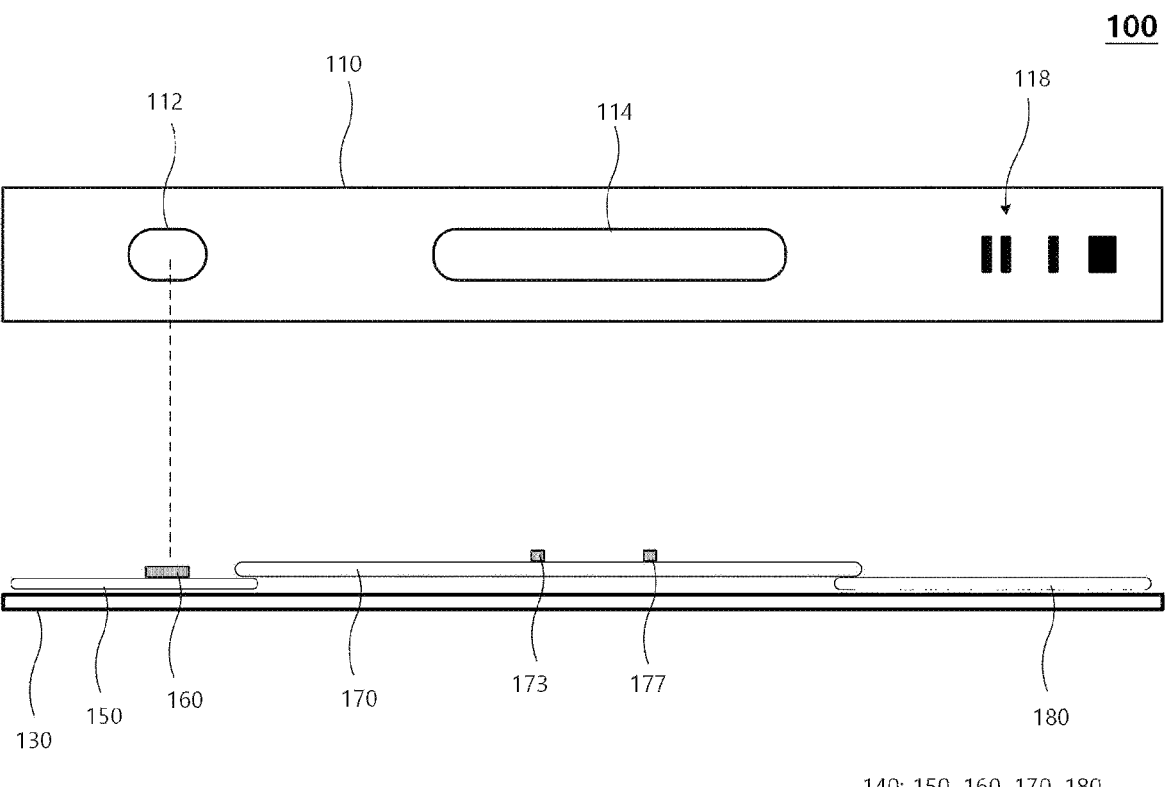
FIG. 3 is a diagram illustrating the upper surface and the interior of a diagnostic cartridge according to a first embodiment of the present disclosure.

FIG. 3 is a diagram illustrating the upper surface and the interior of a diagnostic cartridge according to a first embodiment of the present disclosure.

Figure 4:
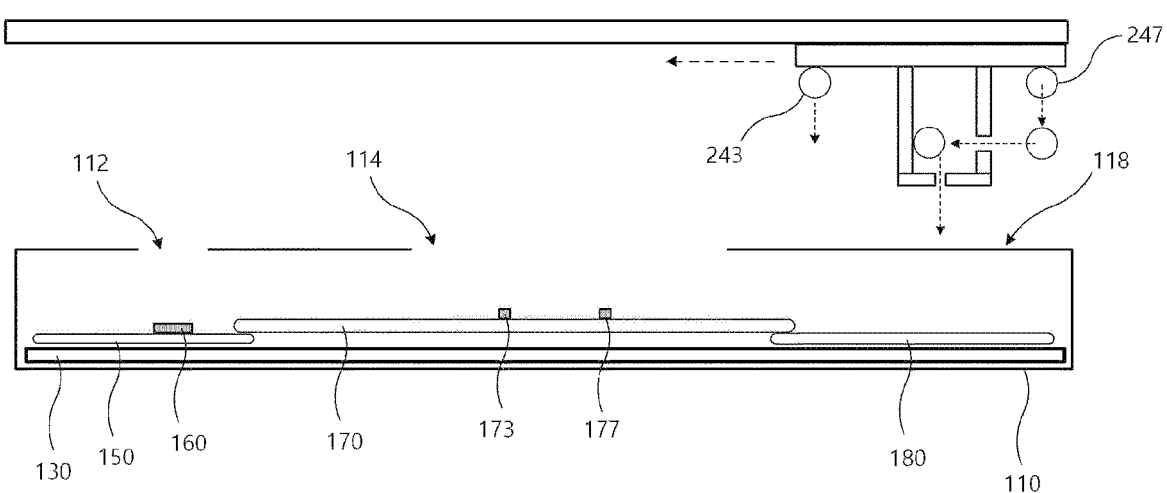
FIG. 4 is a diagram illustrating the operation of the reader when the diagnostic cartridge according to the first embodiment of the present disclosure is inserted.

FIG. 4 is a diagram illustrating the operation of the reader when the diagnostic cartridge according to the first embodiment of the present disclosure is inserted.

Figure 5:
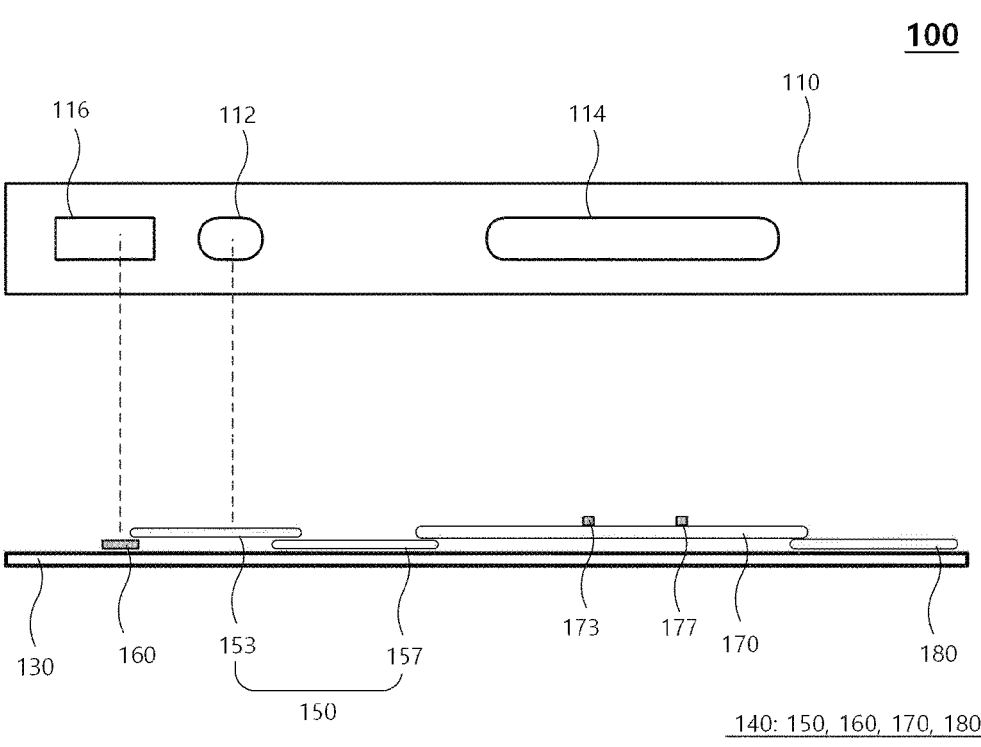
FIG. 5 is a diagram illustrating the upper surface and the interior of a diagnostic cartridge according to a second embodiment of the present disclosure.

FIG. 5 is a diagram illustrating the upper surface and the interior of a diagnostic cartridge according to a second embodiment of the present disclosure.

Figure 6:
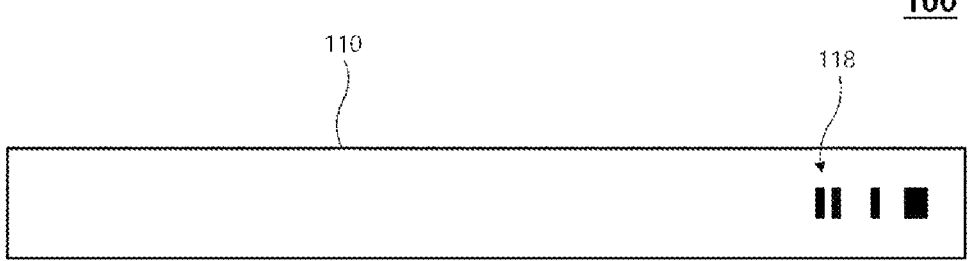
FIG. 6 is a diagram illustrating the lower surface of the diagnostic cartridge according to the second embodiment of the present disclosure.

FIG. 6 is a diagram illustrating the lower surface of the diagnostic cartridge according to the second embodiment of the present disclosure.

Figure 7:
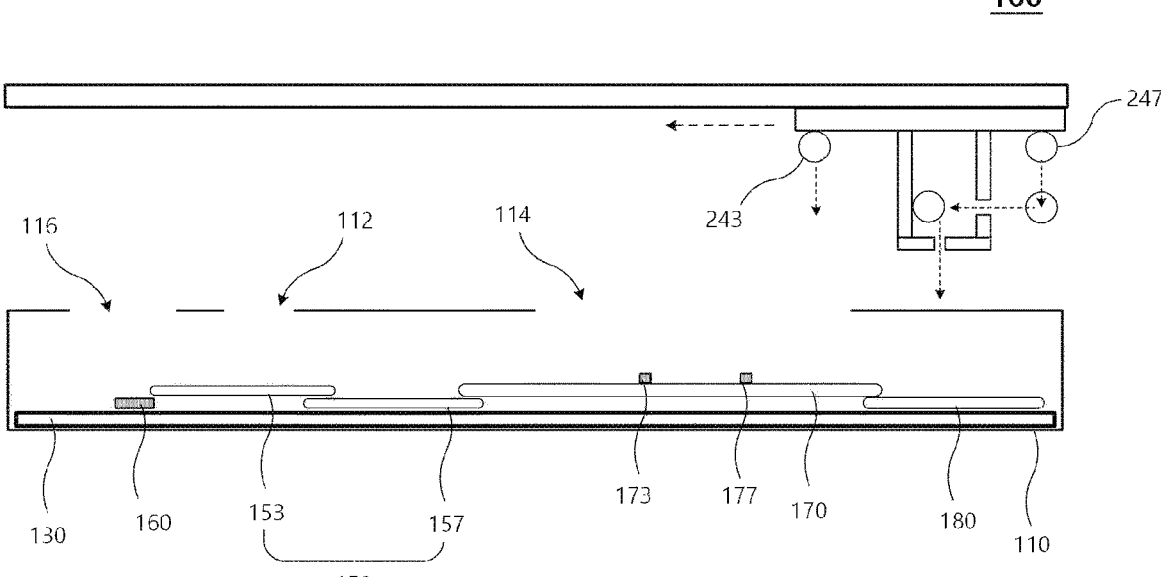
FIG. 7 is a diagram illustrating the operation of the reader when the diagnostic cartridge according to the second embodiment of the present disclosure is inserted.

FIG. 7 is a diagram illustrating the operation of the reader when the diagnostic cartridge according to the second embodiment of the present disclosure is inserted.

Figure 8:
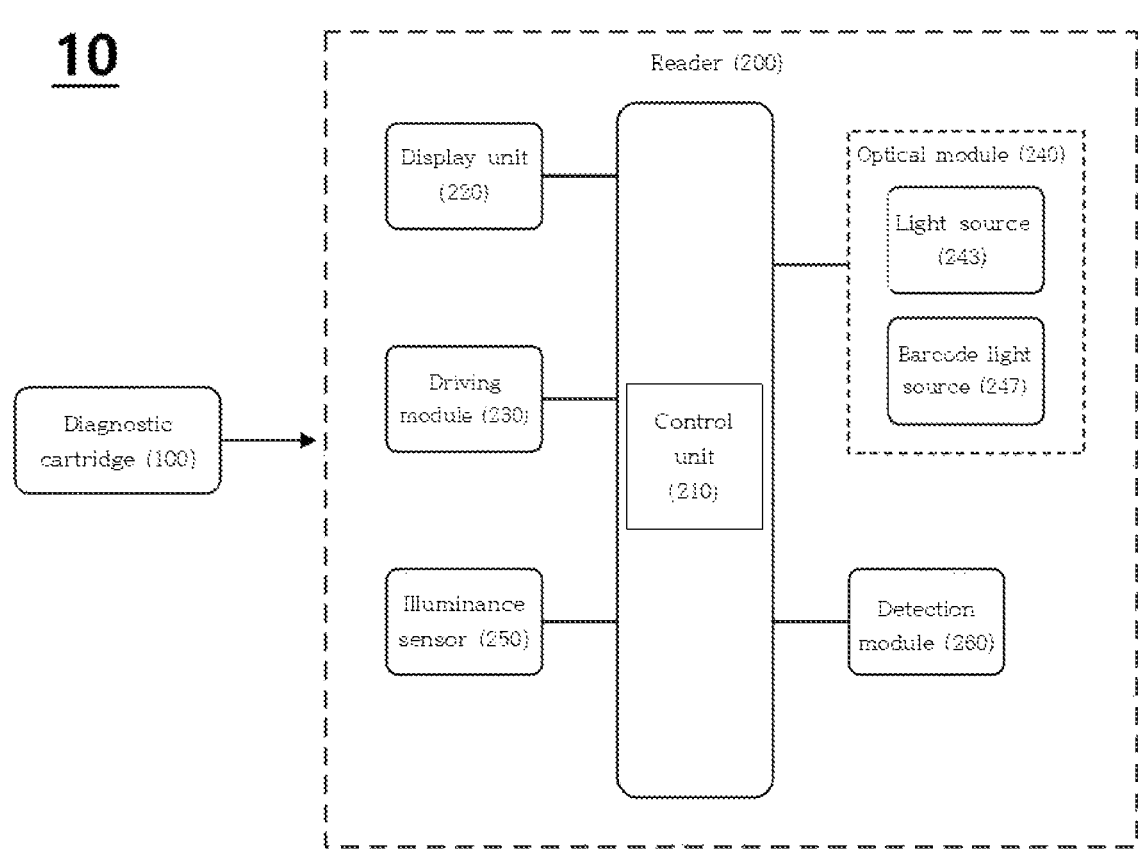
FIG. 8 is a block diagram of an immunodiagnostic system according to an embodiment of the present disclosure.

FIG. 8 is a block diagram of an immunodiagnostic system according to an embodiment of the present disclosure.

In the embodiments of the present disclosure, two types of diagnostic cartridges 100 are exemplified, i.e., as a first embodiment and a second embodiment. However, because the reader 200 changes the control process in one type of reader 200, the reader 200 illustrated in FIG. 8 will be described.

First, referring to FIGS. 3 and 4, a diagnostic cartridge 100 according to the first embodiment of the present disclosure will be described.

The diagnostic cartridge 100 according to the first embodiment of the present disclosure includes a case 110, a support 130, and a pad part 140.

However, in some embodiments, the diagnostic cartridge 100 may include fewer or more components than the components illustrated in FIG. 3.

The case 110 is to cover the internal components, and includes a sample inlet 112, a first window 114 for fluorescence measurement, and a barcode 118 provided at different locations on the upper surface.

The components are preferably formed to be spaced apart from one another at predetermined distances, and in some embodiments, the distances among the components may be differently formed depending on the type of the diagnostic cartridge 100 and the type of a sample to be diagnosed.

The barcode 118 is a means by which the diagnostic cartridge 100 can be identified, and may include information such as the type of the diagnostic cartridge 100, the date of manufacture, the type of a sample being introduced, and so on.

The case 110 may include an upper case and a lower case. The support 130 may be located in the lower case, and the pad part 140 may be formed to be put on the support 130.

The pad part 140 includes a sample pad 150, a coloration pad 160, a diagnostic pad 170, and an absorption pad 180.

The sample pad 150 is arranged to correspond with the location of the sample inlet 112, and one end of the sample pad is arranged to contact the diagnostic pad 170 such that the sample which is introduced into the sample inlet 112 is moved to the diagnostic pad 170.

The coloration pad 160 is arranged on the sample pad 150, and is arranged to correspond with the location of the sample inlet 112, causing a color reaction due to the sample introduced into the sample inlet 112.

Furthermore, due to such configuration and structure, the control unit 210 can control the illuminance sensor 250 to detect the color reaction of the coloration pad 160 through the open sample inlet 112.

The diagnostic pad 170 includes a fluorescent material which can detect fluorescence or luminescence signals when forming an antigen/antibody complex using the antigen/antibody reaction for a quantitative immunological assay reagent, and a fluorescent reaction occurs due to the sample that has moved through the sample pad 150.

As an embodiment, the diagnostic pad 170 may have a test zone and a control zone formed to generate fluorescent signals after an immune reaction.

The control zone can confirm the validity of the reagent reaction by the fluorescence of the control zone when a proper sample reaction occurs, using an antigen/antibody conjugate independent of the antigen of interest in the reagent.

In addition, the test zone is to cause reaction between the antigen of interest in the specimen and the antibody conjugate, and is to cause reaction with another antibody fixed in this area and detect the antigen-antibody complex.

Moreover, the control unit 210 controls the driving module 230 to position the detection module 260 on the first window 114, moves the optical module 240, and detects the fluorescent emission light emitted from the diagnostic pad 170 through the detection module 260.

As described above, the sample introduced into the sample inlet 112 moves to the diagnostic pad 170, and the sample moves to the absorption pad 180 positioned at the end of the pad part 140, thereby ending the movement.

Referring to FIG. 8, the immunodiagnostic reader 200 according to an embodiment of the present disclosure includes a control unit 210, a display unit 220, a driving module 230, an illuminance sensor 250, an optical module 240, and a detection module 260.

However, in some embodiments, the reader 200 may include fewer or more components than the components illustrated in FIG. 8.

The control unit 210 can control the driving module 230 to move the optical module 240, and if it is detected that the diagnostic cartridge 100 is inserted into the insertion part, the control unit 210 starts a diagnosis mode.

The optical module 240 can include a light source 243 which can irradiate light to the cartridge, a light guide unit (not shown) which can guide the light irradiated from the light source 243, an illuminance sensor 250, a detection module 260, and so on.

In this instance, in order to detect the insertion of the diagnostic cartridge 100, an insertion part, a sensor for sensing that the diagnostic cartridge 100 is fully inserted into the insertion space, and a button may be included, and an input/output means may be provided to receive a diagnosis start request from a user.

As described above, since one of various methods of starting a diagnosis may be selected, more detailed description will be omitted.

The control unit 210 controls the driving module 230 to move the barcode light source 247 to the position of the barcode 118 of the diagnostic cartridge 100, and controls the barcode light source 247 to irradiate light in the direction of the barcode 118 with a first light amount.

The control unit 210 recognizes the type of sample based on the light detected from the barcode 118 through the illuminance sensor 250.

Additionally, the control unit 210 controls the driving module 230 to move the barcode light source 247 to the position of the sample inlet 112 of the diagnostic cartridge 100, and controls the barcode light source 247 to irradiate light in the direction of the sample inlet 112 with a second light amount.

In this instance, when irradiating light towards the sample inlet 112, the control unit 210 controls the barcode light source 247 to irradiate light with the second light amount, which is less than the first light amount.

The illuminance sensor 250 may be a barcode sensor having been used in the conventional reader 200. The illuminance sensor 250 can digitize the difference in black and white signals using the barcode light source 247 and sensors.

In this instance, the light coming out from the LED or Laser light source is concentrated on a black/white barcode 118 (identifier) on the surface, and the illuminance sensor 250 detects the scattered light reflected from the barcode 118 to distinguish the intensity of the scattered light.

Using such a principle, the barcode sensor can distinguish the color reaction by detecting the difference in scattered light of the coloring pad 160.

Therefore, the reader 200 can read the barcode and detect the color reaction through the light amount adjustment of the illuminance sensor 250.

The control unit 210 controls the driving module 230 to move the light source 243 to the position of the first window 114, and controls the light source 243 to irradiate light in a direction of the first window 114.

Furthermore, the control unit 210 detects the fluorescent emission light emitted from the diagnostic pad 170 through the detection module 260.

In an embodiment, the driving module 230 includes a motor and a drive shaft for moving the optical module 240, and the control unit 210 controls the driving module 230 to move the optical module 240, recognizes the type of the sample and the type of the diagnostic cartridge 100 based on the light detected from the barcode 118, loads location information of the sample inlet 112 and the first window 114 according to the recognized type of the cartridge, and controls the driving module 230 based on the loaded location information.

Through the above-mentioned configuration, the immunodiagnostic system 10 according to an embodiment of the present disclosure can detect both of the fluorescent reaction and the color reaction by using the conventional reader 200 as it is, and output diagnosis results based on the detection result.

Next, referring to FIGS. 5 to 7, a diagnostic cartridge 100 according to a second embodiment of the present disclosure will be described.

The diagnostic cartridge 100 according to the second embodiment of the present disclosure includes a case 110, a support 130, and a pad part 140.

However, in some embodiments, the diagnostic cartridge 100 may include fewer or more components than the components illustrated in FIG. 5.

The case 110 covers the internal components, and has a sample inlet 112, a first window 114 for fluorescent measurement, and a second window 116 for color measurement, which are formed at different locations on the top surface of the case, and a barcode 118 is formed on the lower surface.

Unlike the first embodiment, the diagnostic cartridge 100 according to the second embodiment is exemplified as having a barcode 118 formed on the lower surface of the diagnostic cartridge 100, but is not limited to thereto. In some embodiments, the barcode 118 may be formed on the upper surface of the diagnostic cartridge 100.

The sample inlet 112, the first window 114, and the second window 116 are preferably formed at predetermined distance intervals, and in some embodiments, the distances of the components may vary depending on the type of the diagnostic cartridge 100 and the type of the sample to be diagnosed.

The barcode 118 is a means by which the diagnostic cartridge 100 can be identified, and may include information such as the type of the diagnostic cartridge 100, the date of manufacture, the type of a sample being introduced, and so on.

The case 110 may include an upper case and a lower case. The support 130 may be located in the lower case, and the pad part 140 may be formed to be put on the support 130.

The pad part 140 includes a sample pad 150, a coloration pad 160, a diagnostic pad 170, and an absorption pad 180.

The sample pad 150 is arranged to correspond with the location of the sample inlet 112, and has one end which is in contact with the coloration pad 160, and the other end which is in contact with the diagnostic pad 170, such that the sample inserted into the sample inlet 112 can move to the coloration pad 160 and the diagnostic pad 170.

More specifically, the sample pad 150 includes a first sample pad 153 arranged at a position corresponding to the position of the sample inlet 112 to allow the inserted sample to move to the coloration pad 160 placed at one end, and a second sample pad 157 arranged at the other end of the first sample pad 153 and arranged to be in contact with the end of the diagnostic pad 170.

The second sample pad 157 serves as a sample distribution pad, which enables the sample moved through the first sample pad 153 to move to the diagnostic pad 170.

The coloration pad 160 is arranged to correspond to the position of the second window 116, and a color reaction occurs due to the sample moved through the sample pad 150.

Due to such configuration and structure, the control unit 210 can control the illuminance sensor 250 to detect the color reaction of the coloration pad 160 through the open sample inlet 112.

The diagnostic pad 170 includes a fluorescent material which can detect fluorescence or luminescence signals when forming an antigen/antibody complex using the antigen/antibody reaction for a quantitative immunological assay reagent, and a fluorescent reaction occurs due to the sample that has moved through the sample pad 150.

In addition, the control unit 210 controls the driving module 230 to locate the detection module 260 on the first window 114, moves the optical module 240, and detects the fluorescent emission light emitted from the diagnostic pad 170 through the detection module 260.

As described above, the sample inserted into the sample inlet 112 moves to the diagnostic pad 170, and the sample moves to the absorption pad 180 located at the end of the pad part 140, such that the movement ends.

When detecting that the diagnostic cartridge 100 has been inserted into the insertion part, the control unit 210 initiates the diagnostic mode.

In this instance, in order to detect the insertion of the diagnostic cartridge 100, an insertion part, a sensor for sensing that the diagnostic cartridge 100 is fully inserted into the insertion space, and a button may be included, and an input/output means may be provided to receive a diagnosis start request from a user.

As described above, since one of various methods of starting a diagnosis may be selected, more detailed description will be omitted.

The control unit 210 controls the driving module 230 to move the barcode light source 247 to the position of the barcode 118 of the diagnostic cartridge 100, and controls the barcode light source 247 to irradiate light in the direction of the barcode 118 with a first light amount.

In this instance, the reader 200 having a pin hole may make the light irradiated from the barcode light source 247 face the barcode 118 formed on the lower surface of the diagnostic cartridge 100.

The control unit 210 recognizes the type of sample based on the light detected from the barcode 118 through the illuminance sensor 250.

Additionally, the control unit 210 controls the driving module 230 to move the barcode light source 247 to the position of the second window 116 of the diagnostic cartridge 100, and controls the barcode light source 247 to irradiate light in the direction of the second window 116 with a second light amount.

In this instance, when irradiating light towards the second window 116, the control unit 210 controls the barcode light source 247 to irradiate light with the second light amount, which is less than the first light amount.

The illuminance sensor 250 may be a barcode sensor having been used in the conventional reader 200. The illuminance sensor 250 can digitize the difference in black and white signals using the barcode light source 247 and sensors.

In this instance, the light coming out from the LED or Laser light source is concentrated on a black/white barcode 118 (identifier) on the surface, and the illuminance sensor 250 detects the scattered light reflected from the barcode 118 to distinguish the intensity of the scattered light.

Using such a principle, the barcode sensor can distinguish the color reaction by detecting the difference in scattered light of the coloration pad 160.

The barcode 118 can be accurately recognized even if the light quantity is high since being differentiated by black and white. However, the coloration pad 160 may be deteriorated in accuracy if the light quantity is above a certain level. Therefore, the coloration pad 160 can detect the color reaction accurately by irradiating light with a second light quantity that is lower than the first light quantity used for the barcode 118.

The controller 210 controls the driving module 230 to move the light source 243 to the position of the first window 114, and controls the light source 243 to irradiate light in the direction of the first window 114.

Furthermore, the control unit 210 detects the fluorescent emission light emitted from the diagnostic pad 170 through the detection module 260.

In an embodiment, the driving module 230 includes a motor and a drive shaft for moving the optical module 240, and the control unit 210 controls the driving module 230 to move the optical module 240, recognizes the type of the sample and the type of the diagnostic cartridge 100 based on the light detected from the barcode 118, loads location information of the first window 114 and the second window 116 according to the recognized type of the cartridge, and controls the driving module 230 based on the loaded location information.

Through the above-mentioned configuration, the immunodiagnostic system 10 according to an embodiment of the present disclosure can detect both of the fluorescent reaction and the color reaction by using the conventional reader 200 as it is, and output diagnosis results based on the detection result.

In an embodiment of the present disclosure, the optical module 240 may include a light guide unit capable of guiding light irradiated from the light source 243. The light guide unit may further include a light source 243 lens capable of condensing light irradiated from the light source 243, at least one mirror capable of reflecting the condensed light, a downward lens, a detection lens for the detection module 260, and a pinhole.

Furthermore, in an embodiment of the present disclosure, the optical module 240 may include a barcode light guide unit capable of guiding light irradiated from the barcode light source 247. The barcode light guide unit may guide light generated from the barcode light source 247 to the barcode 118 of the diagnostic cartridge 100 and guide ambient light from the barcode 118 to be incident on the illuminance sensor 250.

Additionally, the reader 200 may include a downward pinhole and a downward reflective member to irradiate light to the barcode 118 formed on the lower surface of the diagnostic cartridge 100 when the diagnostic cartridge 100 of the second embodiment is inserted.

In an embodiment of the present disclosure, the reader 200 may further include a reference position detection module 260 capable of detecting the positions of the components of the diagnostic cartridge 100 such as the sample inlet 112, the first window 114, and the second window 116. The control unit 210 can also control the driving module 230 based on the results detected through the reference position detection module 260.

In an embodiment, once the type of the sample and the type of the diagnostic cartridge 100 are identified based on the light detected from the barcode 118, the control unit 210 can load the diagnostic algorithm.

Furthermore, the control unit 210 performs a diagnosis on the color reaction of the color pad 160 detected through the illuminance sensor 250 and the fluorescent emission light detected through the detection module 260 using the diagnostic algorithm, and can output the diagnostic result to the display unit 220 or an external device.

Figure 9:
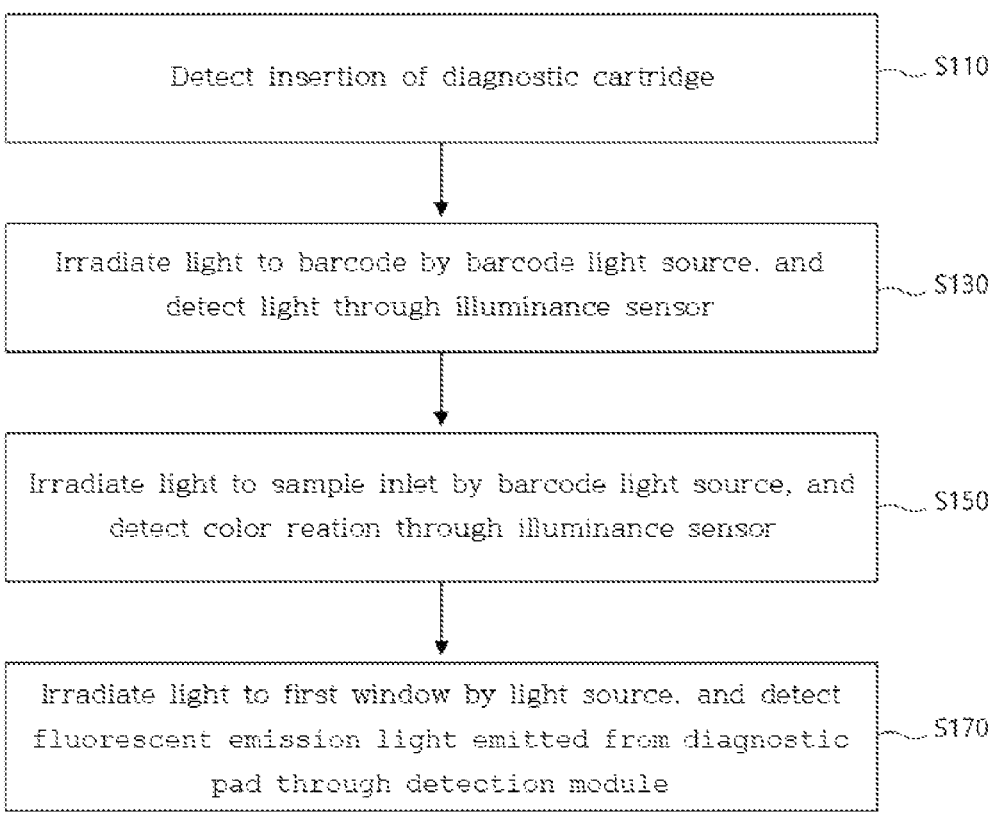

FIGS. 9 and 10 are flow charts of an immunodiagnostic method according to an embodiment of the present disclosure.

FIG. 9 illustrates the process of the immunodiagnostic method when the diagnostic cartridge 100 of the first embodiment is inserted into the reader 200, and FIG. 10 illustrates the process of the immunodiagnostic method when the diagnostic cartridge 100 of the second embodiment is inserted into the reader 200.

Referring to FIG. 9, the control unit 210 of the reader 200 detects the insertion of the diagnostic cartridge 100 (S110).

Next, the control unit 210 controls the driving module 230 to move the barcode light source 247 to the position of the barcode 118 of the diagnostic cartridge 100, and after controlling the barcode light source 247 to irradiate light to the barcode 118, the control unit 210 detects the light detected from the barcode 118 through the illuminance sensor 250 (S130).

Moreover, the control unit 210 recognizes the type of the sample and the type of the diagnostic cartridge 100 based on the light detected from the barcode 118.

Next, the control unit 210 controls the driving module 230 to move the barcode light source 247 to the position of the sample inlet 112, and after controlling the barcode light source 247 to irradiate light to the sample inlet 112, the control unit 210 detects the color reaction of the color pad 160 through the illuminance sensor 250 (S150).

Then, the control unit 210 controls the driving module 230 to move the light source 243 to the position of the first window 114, and after controlling the light source 243 to irradiate light to the first window 114, the control unit 210 detects the fluorescent emission light emitted from the diagnostic pad 170 through the detection module 260 (S170).

Referring to FIG. 10, the control unit 210 of the reader 200 detects the insertion of the diagnostic cartridge 100 (S210).

Next, the control unit 210 controls the driving module 230 to move the barcode light source 247 to a position where the barcode light source 247 can irradiate light to the barcode 118 of the diagnostic cartridge 100, and after controlling the barcode light source 247 to irradiate light in the direction of the barcode 118, the control unit 210 detects the light detected from the barcode 118 through the illuminance sensor 250 (S230).

Furthermore, the control unit 210 recognizes the type of the sample and the type of the diagnostic cartridge 100 based on the light detected from the barcode 118.

Then, the control unit 210 controls the driving module 230 to move the barcode light source 247 to the position of the second window 116, and after controlling the barcode light source 247 to irradiate light to the second window 116, the control unit 210 detects the color reaction of the color pad 160 through the illuminance sensor 250 (S250).

Next, the control unit 210 controls the driving module 230 to move the light source 243 to the position of the first window 114, and after controlling the light source 243 to irradiate light to the first window 114, the control unit 210 detects the fluorescent emission light emitted from the diagnostic pad 170 through the detection module 260 (S270).

The immunodiagnostic method according to the embodiments of the present disclosure described above differs only in the category of the invention from the immunodiagnostic system 10 described through FIGS. 1 to 8, and since the content of the immunodiagnostic method is the same as the immunodiagnostic system 10, so redundant descriptions and examples will be omitted.

The method according to an embodiment of the present disclosure can be implemented as a program (or application) to be executed by being combined with a server which is hardware, and can be stored in a medium.

The program may include code coded as a computer language, such as C, C++, Java, machine language, etc. which a processor (CPU) of the computer can read through a device interface of a computer. The code may include a functional code associated with a function that defines necessary functions for executing the methods, and may include an execution procedure-related control code in which the processor of the computer needs to execute the functions according to predetermined procedures. In addition, the code may further include additional information necessary for the processor of the computer to execute the functions or memory reference-related code for whether the media should be referenced in which location (address) of the internal or external memory of the computer. Moreover, if communication with any other computer or server in a remote location is required to execute the functions by the process of the computer, the code may further include communication-related code for how to communicate with any other computer or server at a remote location using the communication module of the computer, or whether or not any information or media should be transmitted and received in the communication.

The medium to be stored refers not to a medium storing data for a short time but to a medium that stores data semi-permanently, like a register, cache, memory, and the like, and means a medium readable by a device. In detail, as examples of the medium to be stored, there are read-only memories (ROMs), random access memories (RAMs), CD-ROMs, magnetic tapes, floppy disks, optical data storage devices, and the likes, but the present disclosure is not limited thereto. That is, the program can be stored in various recording media on a variety of servers that can be accessed by a computer or various recording media on the user's computer. Furthermore, the media can store code that is distributed to a computer system connected to the network and that is readable by the computer in a distributed fashion.

The method or algorithm described in relation to the embodiments of the present disclosure can be directly embodied in hardware, can be embodied in a software module executed by hardware, or can be embodied by combination thereof. The software module can reside in a random access memory (RAM), a read-only memory (ROM), an erasable programmable read-only memory (EPROM), an electrically erasable programmable read-only memory (EEPROM), a flash memory, a hard disk, a detachable disk, a CD-ROM, or a medium readable by a computer, well-known in the technical field to which the present disclosure belongs.

The above description is only exemplary, and it will be understood by those skilled in the art that the disclosure may be embodied in other concrete forms without changing the technological scope and essential features. Therefore, the above-described embodiments should be considered only as examples in all aspects and not for purposes of limitation.

Advantageous Effects

According to the present disclosure, the diagnostic cartridge, including the diagnostic pad and the color reaction pad can detect a color reaction and a fluorescence reaction through the single diagnostic cartridge.

In addition, according to the present disclosure, the diagnostic cartridge can detect the barcode of the diagnostic cartridge and detect the color reaction of the color pad using one barcode light source.

Furthermore, the present disclosure can use one barcode light source for multiple purposes by adjusting the light quantity when the barcode light source detects the barcode and when the barcode light source detects the color reaction of the color pad.

The advantages of the present disclosure are not limited to the above-mentioned advantages, and other advantages, which are not specifically mentioned herein, will be clearly understood by those skilled in the art from the following description.

The invention claimed is:

1. An immunodiagnostic system performing immunodiagnosis using a diagnostic cartridge inserted into a reader, comprising:
a diagnostic cartridge; and
a reader,
wherein the diagnostic cartridge comprises:
sample inlets located in different positions on the upper surface;
a case having a first window for fluorescence measurement and a barcode; and
a pad part located on a support within the case,
wherein the pad part comprises:
a sample pad allowing a sample inserted into the sample inlet to move;
a coloration pad arranged to correspond to the position of the sample inlet on the sample pad; and
a diagnostic pad located at the end of the sample pad and arranged to correspond to the position of the first window to detect emitted fluorescence,
wherein the reader comprises:
an insertion space into which the diagnostic cartridge is inserted;
a driving module moving an optical module, including a light source and a barcode light source located in different positions; and
a control unit, which when insertion of the diagnostic cartridge into the insertion space is detected, controls the driving module to move the barcode light source to the barcode position of the diagnostic cartridge to control irradiation of a first amount of light toward the barcode, recognizes a type of the diagnostic cartridge and a type of the sample based on the light detected from the barcode through an illuminance sensor, loads position information of the sample inlet and the first window according to the recognized type of the diagnostic cartridge, controls the driving module to move the barcode light source to the position of the sample inlet corresponding to the sample pad position of the diagnostic cartridge to control irradiation of a second amount of light, which is less than the first amount, in a direction of the sample inlet, and detects the color reaction of the coloration pad through the illuminance sensor.

2. The system according to claim 1, wherein after detecting the color reaction of the coloration pad, the control unit controls the driving module to move the light source to the position of the first window, which corresponds to the position of the diagnostic pad in the diagnostic cartridge, and controls it to irradiate light toward the first window, and detects the fluorescence emitted from the diagnostic pad.

3. The system according to claim 2, wherein the diagnostic pad includes a fluorescent material, which can detect fluorescent signals or luminescent signals when an antigen-antibody complex is formed using an antigen-antibody reaction for a quantitative immunoassay reagent, and a fluorescent reaction is caused by the sample moved through the sample pad.

4. The system according to claim 1, wherein the insertion space includes a sensor which detects the insertion of the diagnostic cartridge, and the optical module further includes a light guide unit to guide light irradiated from the light source.

5. The system according to claim 1, wherein the pad part further includes an absorption pad arranged to contact the other end of the diagnostic pad.

6. An immunodiagnostic system performing immunodiagnosis using a diagnostic cartridge inserted into a reader, comprising:
a diagnostic cartridge; and
a reader,
wherein the diagnostic cartridge comprises:
first windows for fluorescence measurement, located in different positions on the upper surface;
a case having a second window for coloration measurement, a sample inlet for inserting sample and a barcode; and
a pad part located on a support within the case,
wherein the pad part comprises:
a diagnostic pad arranged to correspond to the position of the first window;
a coloration pad arranged to correspond to the position of the second window; and
a sample pad which enables the sample inserted into the sample inlet to move toward the coloration pad and the diagnostic pad,
wherein the reader comprises:
an insertion space into which the diagnostic cartridge is inserted;
a driving module moving an optical module, including a light source and a barcode light source located in different positions; and
a control unit, which when insertion of the diagnostic cartridge into the insertion space is detected, controls the driving module to move the barcode light source to the barcode position of the diagnostic cartridge to control irradiation of a first amount of light toward the barcode, recognizes a type of the diagnostic cartridge and a type of the sample based on the light detected from the barcode through an illuminance sensor, loads position information of the first window and the second window according to the recognized type of the diagnostic cartridge, controls the driving module to move the barcode light source to the position of the second window corresponding to the coloration pad position of the diagnostic cartridge to control irradiation of a second amount of light, which is less than the first amount, in a direction of the second window, and detects the color reaction of the coloration pad through the illuminance sensor.

7. The system according to claim 6, wherein after detecting the color reaction of the coloration pad, the control unit controls the driving module to move the light source to the position of the first window, which corresponds to the position of the diagnostic pad in the diagnostic cartridge, and controls it to irradiate light toward the first window, and detects the fluorescence emitted from the diagnostic pad.

8. The system according to claim 7, wherein the diagnostic pad includes a fluorescent material, which can detect fluorescent signals or luminescent signals when an antigen-antibody complex is formed using an antigen-antibody reaction for a quantitative immunoassay reagent, and a fluorescent reaction is caused by the sample moved through the sample pad.

9. The system according to claim 6, wherein the insertion space includes a sensor which detects the insertion of the diagnostic cartridge, and the optical module further includes a light guide unit to guide light irradiated from the light source.

10. The system according to claim 6, wherein the sample pad has one end arranged to contact the coloration pad and the other end arranged to contact the diagnostic pad, such that the sample inserted into the sample inlet is moved to coloration pad and the diagnostic pad.

11. The system according to claim 10, wherein the sample pad comprises:

a first sample pad, which is disposed in a position corresponding to the position of the sample inlet and allows a sample inserted into the sample inlet to move to the coloration pad, which is placed to contact a lower portion of one end; and a second sample pad, of which one end is arranged to contact a lower portion of the other end of first sample pad and the other end is arranged to contact one end of the diagnostic pad, and wherein the pad part further comprises an absorption pad arranged to contact the other end of the diagnostic pad.

* * * * *